United States Patent
Woody

(10) Patent No.: US 10,046,137 B2
(45) Date of Patent: Aug. 14, 2018

(54) METHOD FOR MAINTENANCE OF URETHRAL CATHETERS

(71) Applicant: AVADIM TECHNOLOGIES, INC., Asheville, NC (US)

(72) Inventor: Stephen Thomas Woody, Asheville, NC (US)

(73) Assignee: AVADIM TECHNOLOGIES, INC., Asheville, NC (US)

( * ) Notice: Subject to any disclaimer, the term of this patent is extended or adjusted under 35 U.S.C. 154(b) by 286 days.

(21) Appl. No.: 14/629,320

(22) Filed: Feb. 23, 2015

(65) Prior Publication Data

US 2015/0343172 A1    Dec. 3, 2015

Related U.S. Application Data

(60) Provisional application No. 61/943,287, filed on Feb. 21, 2014, provisional application No. 62/082,019, filed on Nov. 19, 2014.

(51) Int. Cl.
    *A61M 25/00* (2006.01)
    *A61L 2/00* (2006.01)

(52) U.S. Cl.
    CPC ....... *A61M 25/0017* (2013.01); *A61L 2/0088* (2013.01); *A61M 2025/0019* (2013.01);
    (Continued)

(58) Field of Classification Search
    CPC ................ A61M 25/0017; A61M 2025/0019
    See application file for complete search history.

(56) References Cited

U.S. PATENT DOCUMENTS 3,557,006 A    1/1971  Ferrara et al.
4,784,647 A   11/1988  Gross
(Continued)

FOREIGN PATENT DOCUMENTS

GB    2481456 A     12/2011
GB    2511350 A      9/2014
WO    2013/142374 A1  9/2013

OTHER PUBLICATIONS

Burnett et al, Stategies to Prevent Urinary Tract Infection from Urinary Catheter Insertion in the Emergency Department, Dec. 9, 2009, Journal of Emergency Nursing, vol. 36 Issue 6, p. 548.*
(Continued)

*Primary Examiner* — Adam Marcetich
*Assistant Examiner* — Jessica Arble
(74) *Attorney, Agent, or Firm* — Pedigo Law Firm PLLC; Paul Pedigo; Heather Medd Seitz

(57) ABSTRACT

A method for insertion, maintenance, and removal of urethral catheters in mammals including humans includes steps for preventing or reducing the incidence of catheter associated urinary tract infections. In addition to sterile procedures currently practiced or as may be practiced in the future in connection with catheter use, the method includes the steps of applying an antiseptic, zwitterionic, and acidic skincare solution capable of preserving the stratum corneum to the perineum, meatus, and contiguous mucosa surrounding the insertion site before insertion, after insertion, periodically during the period of indwelling, in connection with any incidence of incontinence, and, optionally, before and after removal of the catheter. Application of the solution optionally is continued after catheter removal on a periodic basis until the threat of an infection associated with catheter use has passed, typically at least about five (5) to seven (7) days
(Continued)

and up to thirty (30) days. The solution pH is desirably from about 4.4 to 5.5.

12 Claims, 5 Drawing Sheets

(52) U.S. Cl.
CPC .. *A61M 2025/0056* (2013.01); *A61M 2210/14* (2013.01); *A61M 2210/16* (2013.01)

(56) References Cited

U.S. PATENT DOCUMENTS

| | | | |
|---|---|---|---|
| 5,702,992 A | 12/1997 | Martin et al. | |
| 5,902,283 A | 5/1999 | Darouiche | |
| 6,231,875 B1 | 5/2001 | Sun et al. | |
| 6,358,516 B1* | 3/2002 | Harod | A61K 8/0208 424/401 |
| 6,498,157 B2 | 12/2002 | Sodemann | |
| 7,635,358 B2 | 12/2009 | Tan | |
| 7,947,021 B2 | 5/2011 | Bourne et al. | |
| 8,127,922 B2 | 3/2012 | Nordholm et al. | |
| 8,328,792 B2 | 12/2012 | Nishtala et al. | |
| 8,414,547 B2 | 4/2013 | DiFiore et al. | |
| 9,446,090 B2 | 9/2016 | Bevilacqua et al. | |
| 2002/0058010 A1 | 5/2002 | Picard-Lesboueyries et al. | |
| 2002/0103092 A1 | 8/2002 | Tashjian et al. | |
| 2007/0071705 A1 | 3/2007 | De Oliveira et al. | |
| 2007/0244449 A1* | 10/2007 | Najafi | A61K 9/0024 604/265 |
| 2009/0221989 A1 | 9/2009 | Najafi et al. | |
| 2010/0096287 A1 | 4/2010 | Stoesz et al. | |
| 2010/0145251 A1 | 6/2010 | Polaschegg | |
| 2010/0209535 A1 | 8/2010 | Kiani | |
| 2010/0311668 A1 | 12/2010 | Farwick et al. | |
| 2011/0033540 A1 | 2/2011 | Daniloff et al. | |
| 2011/0129552 A1 | 6/2011 | Saha et al. | |
| 2011/0245757 A1 | 10/2011 | Myntti et al. | |
| 2011/0262558 A1 | 10/2011 | Huckfeldt et al. | |
| 2011/0283662 A1 | 11/2011 | Zhang et al. | |
| 2012/0203211 A1 | 8/2012 | Weadock et al. | |
| 2012/0282348 A1 | 11/2012 | Yates et al. | |
| 2012/0282351 A1 | 11/2012 | Najafi et al. | |
| 2013/0006226 A1* | 1/2013 | Hong | A61M 25/0017 604/544 |
| 2013/0085093 A1* | 4/2013 | Ishihara | C11D 3/3765 510/245 |
| 2013/0085469 A1 | 4/2013 | Polaschegg | |
| 2013/0123221 A1 | 5/2013 | Pearlman | |
| 2014/0179640 A1 | 6/2014 | Weinberger et al. | |
| 2016/0158393 A1 | 6/2016 | Woody | |
| 2016/0184220 A1 | 6/2016 | Woody | |
| 2017/0128600 A1 | 5/2017 | Woody | |

OTHER PUBLICATIONS

Vanderbilt University, VUMC Guidelines for Management of Indwelling Urinary Catheters, Jun. 3, 2010, Vanderbilt University Medical Center.*
CDC, Guidelines for Prevention of Catheter-Associated Urinary Tract Infections, 2009, U.S. Department of Health and Human Services.*
Lo et al, Strategies to Prevent Catheter-Associated Urinary Tract Infections in Acute Care Hospitals, Oct. 2008, Infection Control and Hospital Epidemiology, vol. 29, 41-50.*
Safety and Effectiveness of Health Care Antiseptics; Topical Antimicrobial Drug Products for Over-the-Counter Human Use; Proposed Amendment of the Tentative Final Monograph;Reopening of Administrative Record, May 1, 2015, Federal Register, 25165-25205.*
Dermajuv, "Acne Scar Reduction System", Mintel GNPD, Feb. 1, 2010, pp. 1-8.
Centers for Disease Control and Prevention, "Technical Information—HAI and Antibiotic Use Prevalence Survey", Emerging Infections Program—Healthcare-Associated Infections Projects, 2014, 3 pages.
Gould et al., "Guideline for Prevention of Catheter-associated Urinary Tract Infections", Centers for Disease Control, Healthcare Infection Control Practices Advisory Committee, 2009, p. 8, 9; Q2B.1.a; p. 39 (Total 67 pages).
Magill et al., "Multistate Point-Prevalence Survey of Health Care-Associated Infections", The New England Journal of Medicine, vol. 370, No. 13, Published on Mar. 27, 2014, pp. 1198-1208.
International Search Report and Written Opinion received for PCT Application No. PCT/US2015/017151, dated Aug. 11, 2015, 7 pages.
International Search Report and Written Opinion received for PCT Application No. PCT/US2016/038043, dated Sep. 27, 2016, 12 pages.
International Search Report and Written Opinion received for PCT Application No. PCT/US2016/038409, dated Sep. 21, 2016, 10 pages.
Schauer et al., "Bariatric Surgery versus Intensive Medical Therapy for Diabetes—3-Year Outcomes", The New England Journal of Medicine, vol. 370, Mar. 31, 2014, pp. 2002-2013.
Tambyah et al., "The Direct Costs of Nosocomial Catheter-Associated Urinary Tract Infection in the Era of Managed Care", Infection Control & Hospital Epidemiology, vol. 23, Issue 1, 2002, pp. 27-31.
Theraworx, "When Clean is Not Enough", Aug. 1, 2014, 2 pages.
Woody, Stephen, "Method for Maintenance of Urethral Catheters", U.S. Appl. No. 61/943,287, filed Feb. 21, 2014, 25 pages.
Woody, Steve, "Method for the Prevention and Treatment of Acne", U.S. Appl. No. 62/082,019, filed Nov. 19, 2014, 27 pages.
Zeuzem et al., "Sofosbuvir and Ribavirin in HCV Genotypes 2 and 3", The New England Journal of Medicine, vol. 370, No. 21, May 22, 2014, pp. 1993-2001.
International Search Report and Written Opinion received for PCT Patent Application No. PCT/US2015/061581, dated Jul. 18, 2016, 11 pages.
Lynn P. Roser, Emily C. Piercy, and Terry Altpeter, "Targeting zero: One hospital's journey to reduce CAUTI", Nursing Management, Dec. 2014, 3 pages.
Japanese Patent Office, Office Action Translation, dated Aug. 1, 2017, 2 pages.
Bulletin of Kawasaki City College of Nursing, 2007, 12(1), 10 pages.
Firsthealth, FirstHealth Moore Regional Hospital, Pinehurst, NC; Aug. 2013-Oct. 2013; https://www.hpnonline.com/ inside/2014-04/1404-IP-Success.html, 2 pages.
Mosley, G. A. PMF (Pharmaceutical Microbiology Forum) Newsletter; 14(5); pp. 1-15.

* cited by examiner

METHOD FOR MAINTENANCE OF URETHRAL CATHETERS

CROSS REFERENCE TO RELATED APPLICATIONS

This application claims the benefit of U.S. Provisional Application Ser. No. 61/943,287, which was filed in the United States Patent and Trademark Office on Feb. 21, 2014, and is entitled Method for Maintenance of Urethral Catheters, Including Steps up to and after Catheter Removal; and also claims the benefit of U.S. Provisional Application Ser. No. 62/082,019, which was filed in the United States Patent and Trademark Office on Nov. 19, 2014, and is entitled Method for the Prevention and Treatment of Acne; and which incorporates by reference each of these Provisional applications in their entirety.

FIELD OF THE INVENTION

This invention relates to methods for reducing the incidence and severity of catheter-acquired urinary tract infections, also known by the acronym CAUTI's, arising from urethral catheter use, especially prolonged use of indwelling catheters in a hospital or other care setting.

BACKGROUND OF THE INVENTION

Urinary catheters are frequently used in many different areas of hospitals from Intensive Care Units to Labor and Delivery. Hospitals implement sterile protocols specific to urinary catheters to reduce the risk that a patient will develop a hospital-acquired and catheter-associated urinary tract infection. However, CAUTI's remain a significant and costly type of hospital acquired infection ("HAI") and the reasons for CAUTI's are thought to be multifactorial, including patient risk factors, nursing behaviors, data analysis, daily surveillance, catheter materials, and cleansing products.

According to an article written by Dr. Evelyn Lo, M.D. and others entitled "Strategies to Prevent Catheter-Associated Urinary Tract Infections in Acute Care Hospitals," published in the October 2008 issue of the magazine *Infection Control and Hospital Epidemiology* by The University of Chicago Press, page S41, urinary tract infections are the most common of all hospital acquired infections, and 80% of urinary tract infections are attributable to indwelling urethral catheters. The January 2002 issue of the same magazine, in an article by Paul A. Tambyah, MBBS and others entitled "The Direct Costs of Nosocomial Catheter-Associated Urinary Tract Infection in the Era of Managed Care" reports at page 27 that, regardless of the sterile protocols developed for catheter use, CAUTI's still account for more than one million infections in U.S. hospitals each year. Those one million infections result in approximately 13,000 deaths a year from urinary tract infections, according to the Centers for Disease Control as reported in their *Device-associated Module CAUTI*, published in January 2014. Urinary catheters are not only associated with mortality due to CAUTI's, but urinary catheters are also associated with other negative outcomes including nonbacterial urethral inflammation, urethral strictures, medical trauma, morbidity, longer hospital stays, and increased antibiotic use.

Up to half of patients that require the use of an indwelling urethral catheter for five days or longer will develop bacteriuria or candiduria, as reported in "The Direct Costs of Nosocomial Catheter-Associated Urinary Tract Infection in the Era of Managed Care," which was published by The University of Chicago Press in the January 2002 issue of *Infection Control and Hospital Epidemiology*. Candiduria is commonly thought of as a yeast infection. Bacteriuria is the presence of bacteria in the urine that is not associated with urine sample collection. There is a significant danger posed to hospitals by CAUTI's attributed to the presence of bacteriuria because bacteriuria may include a large reservoir of antibiotic-resistant organisms including yeasts, methicillin-resistant *staphylococcus aureus*, vancomycin-resistant enterococci, and multi-resistant, extended spectrum beta-lactamase-producing gram-negative bacteria.

CAUTI's not only produce negative health outcomes for patients, but result in large financial costs on the order of thirty billion dollars annually according to the non-profit Committee to Reduce Infection Deaths in the web-based article "What is RID?" 2013 available from the world wide web at the file "objective" for the site entitled "hospitalinfection" and having the top level domain name ".org" and the file extension SHTML. As more bacteria and other microorganisms become drug-resistant, the human and financial costs can be expected to increase. Hospitals may be expected to bear the expense alone or to use cost shifting or other means to pass this cost along to patients as an uninsured additional cost. As of 2008, the Centers for Medicare and Medicaid Services stopped reimbursing hospitals for the additional costs of care for patients who develop CAUTI's during hospitalization, in part as an incentive to implement steps to reduce the cost of care.

Given the severity of the problem with CAUTI's from both the human and economic loss perspectives, methods and devices have been developed to try to reduce and to combat CAUTI's. Practice in the field has focused on three areas: 1) treating the area of insertion, typically before insertion, with an antiseptic, typically an aqueous solution of povidone and iodine solution, usually a 10% solution and most commonly one of the BETADINE® brand antiseptic povidone/iodine formulations; 2) treating the catheter device, which includes making the catheter out of antimicrobial materials or applying antimicrobial or antiseptic substances to the interior or exterior surface of the catheter, including, for example one of the BETADINE® brand antiseptic povidone/iodine formulations, and 3) treating the bladder and bladder contents to prevent or reduce CAUTI's, typically with antimicrobial compounds, including taurolidine.

Maintenance of the urethral catheter presents unique issues at least in part due to the nature of the surrounding tissues, which includes the more delicate skin of the perineum, urinary meatus, and contiguous mucosa. Hospitals typically employ a sterile procedure for catheter insertion, which includes wiping down the catheter and pre-treating the area where the urethral catheter is to be inserted with an antiseptic compound, usually a povidone-iodine solution such as one of the BETADINE® brand antiseptic povidone/iodine formulations. The 2009 Guidelines for Prevention of Catheter-Associated Urinary Tract Infections published by the Centers for Disease Control ("CDC") specifically notes that there is no documented benefit of antiseptic cleaning regimens before or after catheterization to prevent CAUTI's, as compared to sterile water. Given the high rate of CAUTI's that occur in U.S. hospitals, the common sterile procedures that use antiseptics appear to do little to reduce infection rates as compared to water.

Problems arise in part due to the nature of hospital and emergency room practice. Emergency room procedures are rarely done under ideal conditions, but can influence outcomes much later in a patient's hospital stay. A focus on the immediate, life-sustaining needs of a patient may preclude consideration of longer-term consequences. The pace of emergency room care can result in shortcuts being taken by precluding taking the time to fully follow a recommended protocol before more urgent matters are addressed. For example, incoming patients may already have a urinary tract infection ("UTI") on arrival and under ideal conditions a protocol would be followed to confirm an existing UTI. Sometimes this step is skipped. BETADINE® brand antiseptic povidone/iodine formulations should be allowed to dry for three minutes, which may be too long in an emergency situation, resulting in poor aseptic technique when inserting a catheter. Some patients may not even need a catheter, at least not immediately, and other options may be available for urination. The tendency to catheterize emergency room patients can be further complicated by use of an inappropriate size catheter, rushing to insert the catheter, poor catheter placement, and other factors. Individual intensive care units may have widely varying CAUTI rates as a result and the rates may fluctuate. Increased rates of CAUTI's tend to come in clusters.

Another technique for reducing the opportunity for infection has been to make the catheter body out of antimicrobial materials or to coat the catheters with an antimicrobial substance, including for example, silver. On page 39 of the studies cited by the CDC Guidelines referenced above, silver alloy-coated Foley catheters reduced the risk of asymptomatic bacteriuria compared to a standard latex catheter. The results were more pronounced when the silver coated catheter was indwelling in patients that had to be catheterized for less than one week. However, using a catheter for such a short time frame may not be a viable option for all patients. The 2009 CDC Guidelines refer to "low or very low quality evidence" that suggests a benefit in using an antimicrobial or antiseptic-impregnated Foley catheter and recommends further research.

Once the catheter is inserted, another treatment method proposes that infections can be treated by irrigating the catheter with an antimicrobial compound, or instilling the bladder with the antimicrobial compound through the catheter. Some of the suggested methods use taurolidine, which has antimicrobial properties and can decrease infection rates, but produces intense pain in most tissues at concentrations as low as about 10 mg/ml. Taurolidine is not generally considered a viable option for patients that are conscious during treatment.

The Infectious Disease Society of America published in March of 2009 guidelines for the diagnosis, prevention, and treatment of Catheter-Associated Urinary Tract Infection in adults that discourages routine catheter irrigation with antimicrobials for the purpose of controlling CAUTI's in patients with indwelling catheters. The Guidelines on page 628 note that the data are said to be insufficient to recommend bladder irrigation to reduce CAUTI's. The CDC makes a similar recommendation in their 2009 Guidelines, mentioned above.

Cleansing compounds are problematic for reducing CAUTI's. Many commonly used cleansing compounds are too harsh for the delicate perineal skin, urinary meatus, and mucosa surrounding the insertion site. Generally speaking, antiseptic compounds, including povidone-iodine solution, alcohol, and chlorohexadrine, among others, and even soap and water, are somewhat harsh and their use can be problematic. Alcohol and chlorohexadrine are not recommended for use on delicate mucosa or on the perineum. Although most all of these compounds are capable of reducing potential contaminants, these compounds may actually contribute to subsequent infections by drying the skin or establishing a basic pH, whereas normal skin has a somewhat acidic pH and moisture content that serves a barrier function by limiting growth of microorganisms. Basic pH is believed to promote the growth of microorganisms, particularly when the antimicrobial ingredients have been reduced in effectiveness over time. Stripping the skin of its naturally occurring and protective lipids is believed to create chemical micro-abrasions and cause moisture loss through the epidermis, drying the skin. Contaminants may more readily enter dry, torn skin and cause infection under these conditions. Specialty lotions may be applied to restore the skin, but normally are not as effective as healthy skin.

Despite current methods and devices for reducing CAUTI's, the number of infections and the costs of treatment remain high and problematic for patients and hospitals. The multifactorial nature of the CAUTI problem makes resolution difficult. Still, it would be desirable to develop improved methods for reducing CAUTI's to more manageable levels, which improved methods are less troublesome and more efficient for hospital personnel to accept and implement compared to existing protocols and that are more readily accepted by patients.

SUMMARY OF THE INVENTION

The invention relates to improvements in methods for reducing the frequency of catheter-associated urinary tract infections, commonly referred to by the acronym CAUTI's, which improvements include easily implemented steps for initially decolonizing the delicate perineum, the urinary meatus, and the contiguous mucosa surrounding the catheter insertion site and maintaining these delicate areas in a state that resists infection. The method includes the steps of pre-treatment of the perineum, urinary meatus, mucosa, and the exterior portions of the catheter with a fast-drying antiseptic skin care solution both before and immediately after catheter insertion, followed by continual maintenance treatments with the solution at regular intervals of from about 4 to 12 hours for maintenance of the perineum and exposed portions of the catheter. In addition, treatment is performed after each incidence of bowel incontinence. In some embodiments, treatment is also performed immediately before catheter withdrawal and the perineum, urinary meatus, and contiguous mucosa wiped with soft, lint free cloth impregnated with the solution immediately after withdrawal. Still further embodiments may include post-withdrawal maintenance treatment steps in which the perineum, urinary meatus, and mucosa are continually wiped at regular intervals for a sufficient period of time after withdrawal to reduce or preclude infection attributable to the use of a catheter. Typically, this maintenance step is performed by patient self-care after discharge from a hospital for about five to seven days. It should be understood that patients include pets and other mammals that may be catheterized and that patient self-care is performed by a caregiver.

It should be recognized that by "antiseptic" is meant a substance that kills and prevents growth and reproduction of bacteria, protozoa, yeast, fungi, and viruses. The term "antiseptic" is sometimes used synonymously with "antimicrobial," which is how we used the term here. Antiseptics and antimicrobials should be distinguished from antibiotics, which kill bacteria.

The method of the invention benefits from the use of antimicrobial and antiseptic compounds that typically do not significantly alter the pH of normal skin and support the stratum corneum, in themselves not stripping the skin of lipids or moisture or causing micro-abrasions or tears in the skin and contiguous mucosa. The invention is based at least in part on the recognition that, in addition to or even in place of the treatment that is commonly practiced on sterile insertion of the catheter and during catheter use, especially after an incidence of bowel incontinence, additional treatments are necessary to perform continually at regular intervals to cleanse and to maintain the catheter insertion site throughout use.

Most CAUTI's occur after a period of indwelling of 4 to 5 days, indicating that the primary source of many infections is maintenance, not insertion. The initial cleansing and reduction in infectious agents, along with cleansing after contaminating events, is sometimes referred to as "primary decolonization," and maintenance of the skin thereafter, or at least until the next primary decolonization event, is sometimes referred to as "secondary decolonization." Particularly for patients with indwelling urinary catheters for an extended period of time, of five days or more, an initial primary decolonization followed by secondary decolonization multiple times throughout and after use for a minimum period of time, with occasional additional primary decolonization after a contaminating event, with the cleansers used in accordance with the invention, should greatly reduce incidence of CAUTI's.

It is believed that withdrawal of the catheter could result in micro tears or abrasions in the urethra that can facilitate infection and that continual treatment of the insertion area is desirable following removal of the catheter for a period of time sufficient to promote healing and to reduce or preclude the possibility of infection by promoting the skin's natural defenses, in addition to cleansing and reducing or at least not promoting the growth of potentially infectious microbes.

Thus, solutions used in connection with decolonizing and maintenance of a urinary catheter insertion site should typically be those that preserve the barrier function of the skin, including, minimally, moisture content, lipids, and mildly acidic pH, in addition to having an antimicrobial or antiseptic quality. It is thus desirable to use less harsh antimicrobial or antiseptic compounds that do not damage the skin and contiguous mucosa, that promote a pH level similar to that of normal skin, and that preserve moisture and lipids, although it is believed that the method of the invention could be practiced with other types of compounds, if permitted. It should be recognized that some common antiseptic compounds are not recommended for use on the perineum, among them alcohol and chlorohexadine. Use of such compounds may not be equivalent to those less harsh treatments that preserve the natural barrier function of the skin and mucosa.

Although the invention may be practiced with current sterile insertion techniques that normally rely on at least pre-insertion wiping of the perineum and catheter body with sterile water, povidone-iodine solution, or equivalent antiseptic solutions, it is believed that treatment solely with the method set forth herein in a sterile manner following insertion protocol, may be sufficient to accomplish sterile insertion. Thereafter, sterile methods may be practiced as advised and as reasonably accomplished by the patient after catheter withdrawal, which may include treatment outside the hospital and in the home setting.

Preferably, the pH of the skincare solution used in the practice of the method of the invention is acidic, and should not be so low as to be painful of application nor so high as to promote infection. A preferred suitable range of pH is from about 4.4 to 5.5. The solution is preferably zwitterionic so as not to strip naturally occurring and protective lipids from the skin, allowing the skin to stay hydrated. The solution should be antimicrobial and antiseptic and will typically be non-antibiotic, unnecessary antibiotic use contributing to resistance in bacteria strains. It is especially useful if the solution is capable of maintaining the balance of flora associated with normal skin, even as the flora is reduced. It is also desirable that the solution be easily absorbed through the epidermis and at least into the deep layers of the dermis in the absence of creating micro-abrasions that can provide an entry point for infectious agents. One example of a cleansing solution for use in the practice of the invention is THERAWORX® brand skin cleanser available from Avadim Technologies, Inc. in Asheville, N.C. THERAWORX® brand and similar skin cleansers are described in U.S. Pat. No. 6,358,516, the contents of which are incorporated herein by reference in their entirety.

Thus, the invention provides an easily implemented method for reducing CAUTI rates including steps of pretreatment, maintenance treatment, and, optionally, treatment on catheter withdrawal and maintenance thereafter for a limited time, by applying an antiseptic skin care solution that is fast drying, that dries within as little as 30 seconds, and that is capable of cleansing the delicate perineum and mucosa surrounding the catheter insertion site by decolonizing infectious microbes and maintaining the natural barrier properties of the skin over time.

BRIEF SUMMARY OF THE DRAWINGS

Having described the invention in general terms, reference will now be made to the following drawings.

DETAILED DESCRIPTION OF THE INVENTION

The invention will now be described more fully hereinafter with reference to the drawings summarized above in which are illustrated some, but not all, of the concepts of the invention. Indeed, the invention may be embodied in many different forms and should not be construed as limited to the specific embodiments set forth herein; rather, the embodiments provided in this disclosure are intended to satisfy applicable legal requirements.

Figure 1:
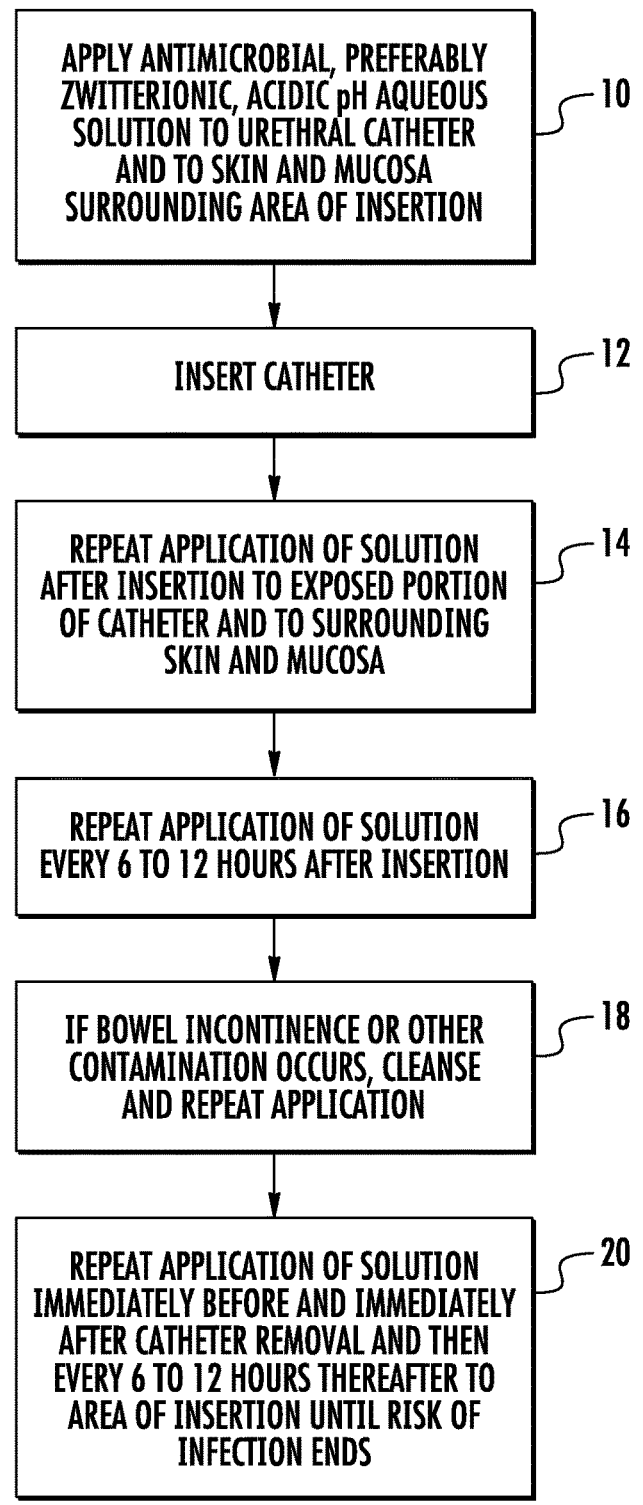
FIG. 1 is a flow diagram of the basic steps of the practice of the method of the invention for the reduction of catheter acquired infections.

FIG. 1 illustrates generally the method steps used in the practice of the invention. In the first step, step number 10, a skin cleansing solution is applied in accordance with the invention to the skin, including the contiguous mucosa, and, optionally and preferably, to the catheter. The catheter typically is sterile; however upon insertion the otherwise sterile catheter may carry infectious microbes into the urethra and bladder. Wiping the catheter with an antiseptic antimicrobial agent is thus preferable. The cleansing solution is preferably also an aqueous solution that is zwitterionic and of acidic pH, so as to preserve the barrier and moisture retention properties of outermost layer of skin. The catheter is wiped with a soft, lint-free cloth that has been saturated with the skin cleansing solution.

The area surrounding the insertion site, typically referred to as the perineum, and including the urinary meatus and contiguous mucosa, is also wiped with a soft, lint-free cloth that is saturated with the skin cleansing solution. It should be recognized that when referring to the area surrounding the insertion site for a urethral catheter as "skin," we also mean to include the contiguous exposed mucosa. It is helpful to provide focused attention to wiping the meatus, which is the entrance to the urethra and is the opening through which urine exits the body. As a general rule, wiping is accomplished front-to-back for women and in concentric circles around glans penis for men. The solution normally should be allowed to dry for thirty seconds and is not rinsed thereafter.

It should be recognized that in a typical sterile insertion technique of the prior art, the perineum is cleansed with soap and water and then a 10% povidone-iodine solution, often Betadine® brand solution, is applied to the perineum, including the meatus. It is desirable that the povidone-iodine solution be allowed to dry for three minutes, although in practice, particularly in emergency room situations, it is believed that the solution typically may not be allowed to dry. The catheter typically is sterile and may not be wiped with the povidone-iodine solution.

The invention may be used in connection with the prior art techniques; normally by performing step 10 as described in FIG. 1 and then applying the povidone-iodine solution either before or after step 10. However, the skin cleansing solution applied in step 10 should not be rinsed with sterile water or otherwise.

Following application of the skin cleansing solution in step 10, and optionally application of a 10% povidone-iodine solution or other solution for use in sterile protocols, with the exception of sterile water, which is not applied after step 10, the catheter is inserted into the urethra. Additional sterile techniques should be practiced, including wearing gloves and the like as is well known to the person of ordinary skill in the art.

After catheter insertion, another soft, lint-free cloth that has been saturated with the skin cleansing solution used in accordance with the invention is wiped around the perineum in accordance with step 14, including the skin and contiguous exposed mucosa, and the exposed portions of the catheter, preferably in a downward direction. Again, as before insertion, wiping is accomplished front-to-back for women and in concentric circles around glans penis for men.

Once insertion and immediate post-insertion catheter care has been accomplished, then catheter maintenance procedures are implemented using the skin cleansing solution in accordance with the invention as set forth in step 16. The catheter should be maintained by continually repeating the application of the skin cleansing solution to the exposed area of the catheter and the surrounding skin at least every 12 hours or more frequently after insertion for the entire period of indwelling time. Depending on specific circumstances or perhaps even an unaccounted cluster of CAUTI's, that time interval between maintenance steps may be reduced to 8, 6, or even 4 hours.

If, during the time the catheter is inserted, one or more incidents of bowel incontinence or other specific contamination occurs, then the patient, including the perineum and exposed portion of the catheter, should be thoroughly cleansed as soon as possible with the skin cleansing solution and the regular, periodic, continual cleansing schedule resumed, all in accordance with step 18. A care decision can be made at this point to reduce the time interval between maintenance steps.

Once a determination has been made that catheterization is no longer required and that the catheter should be removed, then the skin cleansing solution should, optionally, but preferably, be applied again immediately prior to withdrawal to the exposed portions of the catheter and to the perineum as previously accomplished, in accordance with step 20. Further in accordance with step 20, the skin cleansing solution should be applied again, optionally, but preferably, to the perineum immediately after withdrawal, including the meatus, contiguous exposed mucosa, and surrounding skin of the perineum. Thereafter, the skin cleansing solution should, optionally, but preferably, continue to be applied to the perineum, including the meatus, contiguous exposed mucosa, and surrounding skin of the perineum until the danger of infection due to the presence of the catheter is considered to be passed.

It should be recognized that removal of an indwelling catheter can leave micro-abrasions and small tears in the delicate mucosal membranes of the urethra and meatus that provide sites for potential infection. Thus, CAUTI's are believed to occur even after a catheter is technically no longer indwelling, demanding vigilance in treatment until the mucosa has a chance to heal, typically from five to seven days, although treatment could continue for a month, if desired, without harmful side effects from milder skin cleansing solutions preferred for use in the practice of the method steps of the invention. Typically, post-withdrawal treatment, at least after the initial catheter withdrawal, is performed by the patient in self-care in the home setting.

Figure 2:
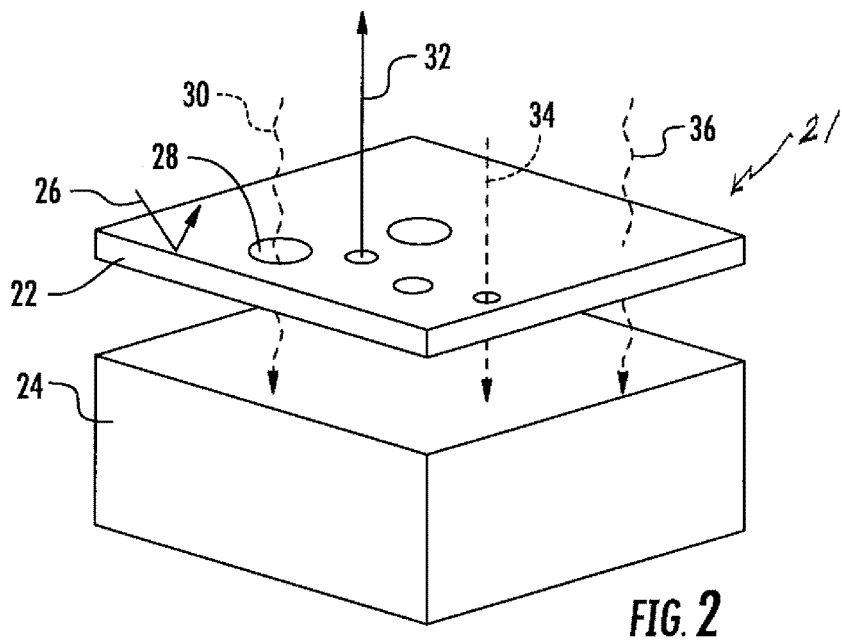
FIG. 2 is a highly schematic exploded perspective view of a section of the skin's layers.

Turning now to a discussion of the skin in its barrier function, FIG. 2 illustrates generally at 21 and in an exploded perspective view a highly schematic section of the skin, including the outer layer, which is the epidermis 22, and the underlying dermis 24. FIG. 2 illustrates flow of various substances through the epidermis to the dermis. At 26, the arrow illustrates the inability of soap and water even to penetrate the epidermis. At 30, the arrow illustrates chlorohexadrine gluconate's ability to create micro abrasions 28 in the epidermis and to penetrate the epidermis through to the dermis. Abrasions damage the skin and allow both water loss as illustrated by the arrow at 32 and potential pathways for infectious agents to penetrate the epidermis and enter the dermis, as illustrated by the arrow at 34.

Chlorohexadrine is not believed to be approved for use on exposed mucosa. Other approved antiseptic, antimicrobial, or antibacterial compounds may be of similar impact in creating micro-abrasions. Although these solutions could potentially be approved for use on mucosa and may thus be used in the practice of the method of the invention, it is not believed that these results would necessarily be equivalent and could ultimately create an environment prone to infection. It should be emphasized that milder solutions as discussed in detail below are preferred, especially those capable of preserving the pH of the skin and its barrier and moisture qualities for an extended period of time, from at least 3 to 12 hours.

Practice of the invention and adherence to catheter maintenance protocol is facilitated by supplying a preferred skincare cleansing solution in kits for sterile insertion of urinary catheters, along with instructions for use, including pre-insertion protocol, twice to six times daily maintenance protocols while the catheter remains inserted, incontinence protocols, withdrawal protocols, and twice to six times daily post-withdrawal protocols, as needed. Cloths typically are preferred for administration of the cleanser, and two-cloth packs have proved useful in trials of the method of the invention, although sprays and foams may also be used. When applying the cleanser from a cloth, it is useful to fold the cloth so as to use a clean fresh cloth surface for each wipe.

The steps of the method can be described as including both primary and secondary decolonization of infectious agents. It should be recognized that by decolonization, what is being described is, as a primary matter, reducing the amount and type of infectious microbes on the skin while maintaining the skin's natural barrier properties, and, as a secondary matter, continuing to maintain or support the skin's natural barrier properties for an extended period of time, including the skin's acidic pH. Although the problem solved immediately herein is directed specifically to CAUTI rates, it should be recognized that similar concepts can also be applied to a number of different areas where active infections occur, including, but not limited to, the treatment of acne, wounds, and other areas of infection on the body, as well as other types of catheters, including intravenous catheters, catheters used in veterinary medicine, decontamination of patients by bathing, and even to decontamination of environmental surfaces, although not necessarily with equivalent results. A modified method may be applied to decolonize patients before they are moved to a new environment or to rooms before a new patient is admitted to the room and includes additional treatments as needed to insure that the opportunity for infection is reduced if not eliminated. Practice of this nature may be especially useful when transferring patients from a hospital to a rehabilitation center, or from a nursing home to a hospital to interrupt the spread of CRE, MRSA, and VRE, which are known to be spread by contaminated patients and can spread infection throughout a hospital or skilled nursing facility and can prove problematic to resolve.

Thus, the basic concepts behind the steps of the method of the invention are suitable for other applications, including other types of indwelling catheters, treatment of acne, which is in reality a small wound and site of bacterial infection, and other wounds or for decolonization of bacteria from entire persons or environments whereby bacterial infections can be prevented or eliminated. These concepts can be incorporated into cleansing protocols using a solution such as is described herein and the protocol altered as needed for continual, regular application of the solution for a sufficient period until the infection or risk of infection has been cleared. Of course, it should be recognized that where no catheter is used, the steps of cleansing the catheter, inserting the catheter, and maintaining the catheter will not be implemented. In a specific embodiment, the skin or other surface is wiped with a cloth pre-moistened with the skincare cleansing agent. Typically, the cloths will be pre-moistened and pre-packaged non-woven wipes. Foam cleansers are also useful and may be more economical.

Turning now to a discussion of the skin's acid mantle, maintaining the effectiveness of the acid mantle promotes good skin health. A damaged acid mantle may lead to a number of skin complaints, such as, dry skin, flaky skin, oil overproduction, sensitivity, and acne. Products that do not facilitate the skin's natural pH can contribute to the degradation of the acid mantle, thereby increasing the likelihood that infections can develop. When the acid mantle is damaged, it can take up to 14 to 17 hours to repair itself, and it is during this time that bacteria can be expected to multiply more effectively. Thus, skin pH is an important component of effectively treating CAUTI's. Practice of the invention and continual adherence to its method to maintain the skin's pH is recommended to reduce and prevent the occurrence and severity of incidents of CAUTI.

The skin is comprised of three primary layers: the epidermis, which is the outermost layer; an intermediate layer, the dermis, comprising hair follicles, pores, sebaceous glands, sweat glands and connective tissue; and the hypodermis, which comprises an insulating fatty layer. The outermost layer, the stratum corneum (SC), is exposed to conditions including temperature and humidity as well as various hygienic care products that can cause damage to this layer. The resulting damage often causes drying of the SC, which can cause the SC to crack, interfere with the normal shedding of skin cells, and prevent the natural healing of damaged cells. The SC comprises dead skin cells and forms an important barrier layer protecting the underlying tissue from infection, dehydration, chemicals, and abrasion. Disruptions to the stratum corneum should be avoided in protocols for indwelling catheter use.

Solutions that are used in connection with the protocols of the invention should typically preserve the barrier function of the skin, components of which are an acidic pH mantle and sustained moisture content, in addition to optionally having antimicrobial and antiseptic properties that address the many types of bacteria that can cause CAUTI's. The acidic pH of the skincare solution used in the practice of the method of the invention can vary from as low as 4.0 to as high as 6.5, which is the range of natural, uninfected skin. The solution is preferably zwitterionic so as not to strip the naturally occurring and protective lipids from the skin, therefore allowing the skin to stay hydrated. The solution is also antimicrobial and antiseptic and will typically be non-antibiotic, unnecessary antibiotic use contributing to resistance in bacteria strains. It is especially useful if the solution is capable of maintaining the balance of flora associated with normal skin, even if the quantity of flora is somewhat reduced. It is also desirable that the solution be easily absorbed through the epidermis and at least into the deep layers of the dermis in the absence of creating microabrasions that can provide and entry point for infectious agents, as illustrated in FIG. 2 at 36.

Cleansing can be accomplished in accordance with the method steps of the invention using a variety of skincare solutions. One aqueous skincare solution that is effective in the practice of the invention is THERAWORX® brand skin cleanser available from Avadim Technologies, Inc. in Asheville, N.C. THERAWORX® brand and similar skin cleansers are described in U.S. Pat. No. 6,358,516, the contents of which are incorporated herein by reference in their entirety.

The solutions for use in the practice of the invention desirably have ingredients for promoting zwitterionic surfactant properties that do not strip the skin of lipids, antimicrobial or at least antiseptic properties, skin penetrating properties, and a mildly acidic pH similar to that of the natural state of the skin and capable of maintaining the normal skin pH over an extended period of time from 3 to 12 hours and indefinitely via regular applications. Antibiotics need not typically be incorporated. Humectants and emollients and agents for promoting healing as taught in U.S. Pat. No. 6,358,516 are desirable.

A skincare and cleansing agent useful in the practice of the invention may include, as described in U.S. Pat. No. 6,358,516, among other ingredients:
(a) at least one surfactant;
(b) at least one anti-inflammatory;
(c) at least one anti-foaming agent;
(d) at least one cell growth-promoting agent;
(e) at least one fast-acting antimicrobial agent, each of said ingredients being skin-compatible and different from the other ingredients of said composition; and at least one different ingredient selected from the group of:
(f) immune system-enhancing agents, wherein at least one immune system-enhancing agent is aloe vera, beta glucan, colloidal silver, or allantoin;
(g) absorption facilitation agents, where in at least one absorption facilitating agent is beta glucan, aloe vera, or colloidal silver;
(h) humectants and emollients, wherein at least one humectant or emollient is aloe vera, vitamin E, or cocamidopropyl;
(i) free radical-scavenging agents, wherein at least one free radical-scavenging agent is a bioflavonoid, a polyphenolic compound, a grapefruit-derived quaternary compound, beta glucan, allantoin, vitamin E, pycnogenol, or grape seed extract; and
(j) healing promoting agents, wherein said ingredients are selected to form a stable, no-rinse, radiation-sterilizable composition that air-dries quickly when applied to the skin and that cleanses, therapeutically conditions, and treats the skin in a one-step application, wherein at least one healing-promoting agent is aloe vera, allantoin, or beta glucan. It should be recognized that where a compound is mentioned in two different categories that the compound serves both functions in the formulation and that each function is present when the compound is present.

Cleansing agents are surfactants, including soaps, including, but not limited to, amphoteric surfactants, which are surfactants having the capacity of behaving either as an acid or a base, including, for example, cocamidopropyl betain, alkyl polyglucosides, lauryl glucoside, and combinations thereof. Reddened skin is the first sign of an infection and other skin problems, and indicates that the skin is redirecting its natural resources from growth and other normal functions to prevention and repair. Reducing or eliminating reddening may increase the growth of healthier new skin. Anti-inflammatory agents include agents that known to reduce skin reddening, including, but not limited to aloe vera, allantoin, cocamidopropyl betain, beta glucan, and combinations thereof, in amounts shown to be effective during cleansing. Skin-compatible anti-foaming agents include silicone-based antifoaming agents, dimethicone copolyol, and the like. When present in the preferred combinations and concentrations, growth-promoting agents promote or stimulate new skin growth and promote healing of significantly greater magnitude than previously observed. Agents that stimulate or promote cell growth, including but not limited to aloe vera, allantoin, which is glyocyldiureide or 5-ureidohydantoin, beta glucan, polyphenolic compounds such as CITRICIDAL® brand grapefruit seed extract, and combinations thereof. CITRICIDAL® brand grapefruit seed extract and like compounds have been demonstrated to be effective against a broad spectrum of bacteria. These compounds contain quaternary compounds derived from grapefruit or other bioflavonoids together with inert ingredients such as glycerin.

Agents that enhance or stimulate the skin's immune system or help provide a secondary immune system, include but are not limited to aloe vera, beta glucan, colloidal silver, allantoin, and combinations thereof. When present in the composition in the preferred quantities, these agents promote healing and also help reduce the incidence of infections.

Colloidal silver, CITRICIDAL® brand grapefruit seed extract, beta glucan, aloe vera, and like ingredients are believed to have therapeutic value to promote and stimulate the existing immune system to help reduce infections and promote healing. Colloidal silver and CITRICIDAL® brand grapefruit seed extract support the natural immune system by reducing its workload; CITRICIDAL® brand grapefruit seed extract is also believed to promote healing by a mechanism which is yet unclear.

Beta glucan, which is a D-glucose polymer also known as beta-1, extract or yeast derivative, is a non-specific immune stimulator that also exhibits free-radical scavenging activity. Beta glucan stimulates the body's immune system T-cells; mannoproteins and polysaccharides such as aloe vera provide the T-cells to be effective. A mannoprotein is a sugar-protein, a glycoprotein, that is linked to beta glucan in yeast and barley cell walls. Mannoproteins directly increase the structural integrity, alertness and numbers of immune cells. Fast-acting, skin-compatible antimicrobial agents are effective against at least one or all of bacteria, viruses, yeasts, and fungi, and include, but not limited to colloidal silver, CITRICIDAL® brand grapefruit seed extract, pycnogenol, grape seed extract, antibiotics, and combinations thereof, in effective amounts to kill infectious organisms, including bacteria, viruses, yeasts, and fungi on and in the skin during skin cleansing and upon drying.

The skin harbors a wide variety of microorganisms; some of these are potentially harmful while others are beneficial. Ideally, this normal bacterial flora is not destroyed by cleansing. However, a cleanser that reduces the accumulation of bacteria and fungi present on the skin helps reduce the incidence of infections, especially in a hospital environment. The selected antimicrobial agent or agents is fast-acting, so as to act against bacteria, fungi, and the like microorganisms. The action of the antimicrobial agent or agents during cleansing and rapid air drying substantially kills viruses, bacteria, fungi, and yeasts present in the living basal cell layer and the dermis of the skin in addition to those transferred onto or living in the dead horny layer or epidermis. This action serves to reduce the occurrence or severity of infections due to bacteria, viruses, and the like infectious microorganisms entering breaks in the skin, whether small tears or micro abrasions.

Some antimicrobial agents, such as colloidal silver and CITRICIDAL® brand grapefruit seed extract, are compatible with normal flora, capable of penetrating into the dermis, and also provide useful antimicrobial properties. Colloidal silver kills single cell microorganisms such as bacteria by penetrating their cell walls in a manner similar to the body's T-cells. Therefore, these organisms cannot mutate into resistant strains as they do with many other antimicrobial agents. However, colloidal silver has limited potency and must preferably be supplemented with other antimicrobial agents in formulating a composition according to the invention. In addition, the colloidal silver is preferably formulated with particles that are small enough to penetrate the dermis, which is approximately 0.005-0.02 microns, and, more preferably, approximately 0.01-0.1 microns.

Numerous studies have demonstrated that CITRICIDAL® brand grapefruit seed extract has many unique and desirable antimicrobial properties, including at least some effectiveness against HIV, hepatitis and other viruses, and a wide range of bacteria, fungi, and yeasts, while being highly biocompatible and providing other benefits to the skin.

Tests show that a combination of 2% or less CITRICIDAL® brand grapefruit seed extract and other agents such as colloidal silver is approximately 99.9% or more effective in killing the harmful microorganisms usually present in the skin, and prevalent in medical institutions.

Compatible humectants and emollients, including but not limited to aloe vera, allantoin, vitamin E (tocopherol), beta glucan, cocamidopropyl betain, and combinations thereof. These agents naturally re-moisturize the dead horny layer, epidermis, and/or dermis without clogging pores.

Humectants and emollients in the composition act to naturally remoisturize the skin surface (i.e., the dermis) to prevent dryness, increase elasticity, reduce the incidence of skin tears, and supplement the activity of the sebaceous glands to reproduce oils without clogging pores. Over usage of humectants and/or emollients is a major cause of skin eruptions, inflammation, and acne, therefore, simply increasing the amounts of humectants and/or emulsifiers to provide a longer lasting protective barrier can promote skin problems. Therefore, the amounts of these ingredients are controlled so as to minimize undesirable effects, particularly regarding the perineum and meatus.

Agents that scavenge free radicals and help detoxify the skin, including but not limited to CITRICIDAL® brand grapefruit seed extract, beta glucan, allantoin, vitamin E, pycnogenol, grape seed extract, and combinations thereof. Agents that promote and/or stimulate new skin growth and skin healing, including but not limited to aloe vera, allantoin, CITRICIDAL® brand grapefruit seed extract, beta glucan, pharmaceuticals, and combinations thereof. Biocompatible preservatives, including but not limited to methylparaben, propylparaben, ethylenediaminetetraacetic acid, which is referred to as EDTA, and like agents and combinations thereof. Biocompatible fragrances, including but not limited to natural orange, lemon, lavender, and combinations thereof. Other beneficial agents, including but not limited to those containing vitamins and vitamin precursors, including vitamin A, carotene, cryptoxanthin, retinol, 3-dehydroretinol, vitamin C or absorbic acid, vitamin E or tocopherol, and the like, herbs, including chamomile, lavender, ginseng, ginkgo, and the like, and antioxidants, collagens, pH-balancing agents, and combinations thereof. Each ingredient of the composition is present in an amount that, as a percentage of the total weight of the composition, is effective either alone or synergistically with the other ingredients to achieve the desired results.

The following examples are provided in support, but not in limitation, of the invention.

EXAMPLES

A trial was conducted at First Health Moore County Regional Hospital, a 395 bed facility, in Pinehurst, N.C. from August to October 2013. Prior to the trial, First Health's CAUTI rate was similar to other similar size hospitals in North Carolina. After reviewing the CAUTI's that occurred at First Health, it was discovered that the majority of CAUTI's occurred after a Foley catheter had been in place for greater than 5 days, which lead the hospital to believe that it had issues with the care and maintenance of catheters. The hospital then used THERAWORX® brand skin cleanser in July of 2013 in its intensive care unit, or ICU, and began the trial in August. Hospital personnel were directed to apply THERAWORX® brand skin cleanser to the perineum as a pretreatment step, both before and immediately after insertion as described hereinabove and to implement a maintenance treatment step every 8 hours while the catheter was inserted.

In the same time period a year earlier the hospital had 4 CAUTI's in the ICU for 1728 catheter days for a rate of 2.3 infections per 1000 catheter days. During the trial in which THERAWORX® brand skin cleanser was used in accordance with the invention, the hospital had 0 CAUTI's in the ICU over 1667 catheter days, which is a rate of 0 infections per 1000 catheter days.

The results of this study were reviewed by hospital ICU staff and the protocol was approved for hospital wide implementation, despite the current best practice recommended in the most recent literature of soap and water.

The policies for catheter insertion and catheter care were reviewed, best evidence based practice was reviewed, and the hospital's policies and protocols were revised in December 2013 for staff to perform catheter care prior to and immediately after insertion and every 8 hours thereafter for the period of indwelling using THERAWORX® brand skin cleanser as a foam on cloths applied to the perineum and catheter, including the additional step of wiping the perineum with THERAWORX® brand skin cleanser after removal of the catheter.

A trial, using THERAWORX® brand skin cleanser, was conducted at five intensive care units at Baptist Hospital, a 383 bed facility in Lexington, Ky. The purpose of the hospital study was to determine whether the use of a colloidal silver impregnated wipe and foam cleanser, which was the THERAWORX® brand skin cleanser, when used as part of a cleansing protocol within the current Foley catheter care protocol practiced by the hospital would be efficacious in reducing the incidence of CAUTI's in the intensive care setting.

Mean infection rates in the five ICU's in 2012 ranged from 1.2 infections per 1000 device days to 5.9 infections per 1000 device days. The hospital performed the steps of the protocol starting in April 2013, including cleansing the perineum prior to insertion with THERAWORX® brand skin cleanser and allowing the solution to dry in air for 30 seconds, opening the sterile Foley catheter and cleansing the Foley catheter with THERAWORX® brand skin cleanser, wiping the meatus with BETADINE® brand antiseptic povidone/iodine formulation, and inserting the catheter using the accepted aseptic techniques. The meatus, perineum, and exposed portions of the catheter were again cleansed with THERAWORX® brand skin cleanser after insertion. Cloths soaked in THERAWORX® brand skin cleanser were used two to three times daily for maintenance wiping and additional wiping was done as a final cleansing for incontinence. As a result, zero CAUTI's were reported in four out of five ICU's by the second month of the study and by the fourth month all five ICU's had reduced their CAUTI infections to zero infections per 1,000 device. Although some units had achieved zero CAUTI infection rates prior to the start of the study, it was only after the study was initiated that all five intensive care units maintained a zero CAUTI infection rate for the same month. These results exceeded the 2012 mean CAUTI rates and were below the National Healthcare Safety Network CAUTI benchmark of 1.4 infections per 1,000 device days.

Figure 3:
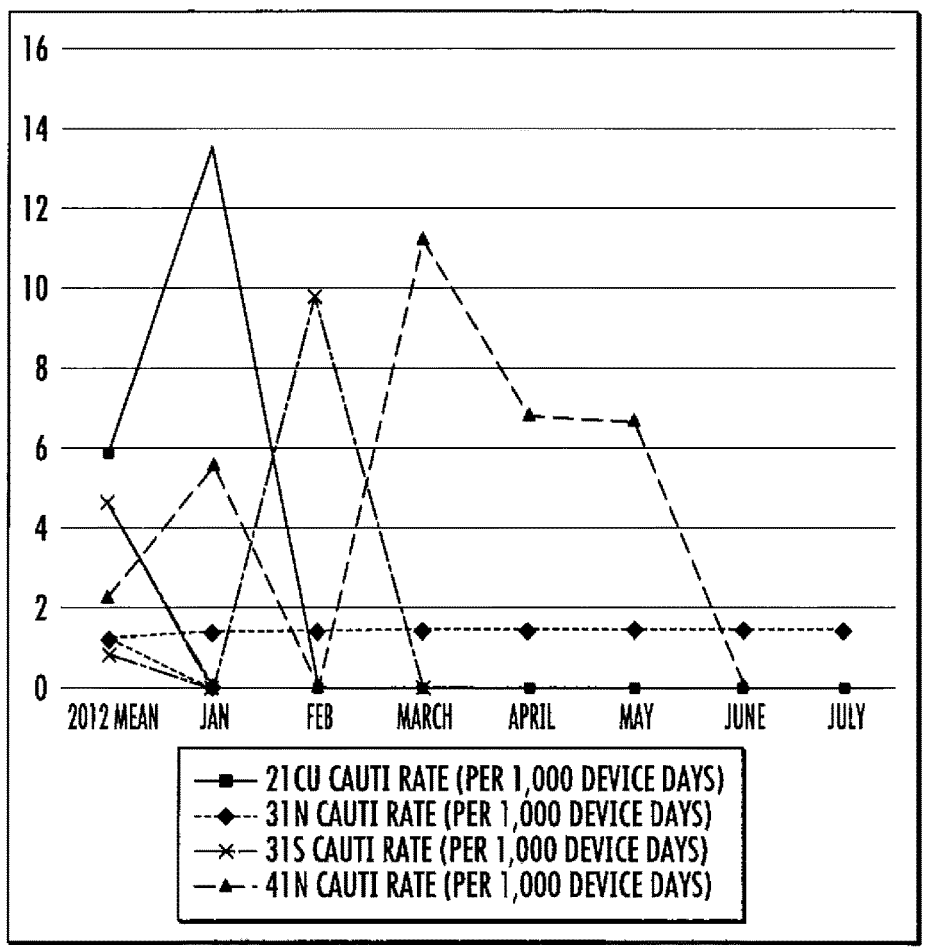
FIG. 3 illustrates the frequency of CAUTI's per 1000 days for the method of the invention compared to existing protocols, taken from a hospital quality improvement project.

Table 1, below, summarizes the results of the hospital study from June 2013 through July 2013 and includes the rates of CAUTI's of each of the five ICU's from January 2013 through July 2013 and the 2012 mean rate of CAUTI's in each of the five ICU's. The corresponding results are illustrated graphically in FIG. 3.

TABLE 1

|  | 2012 Mean | January | February | March | April | May | June | July |
|---|---|---|---|---|---|---|---|---|
| 2ICU CAUTI Rate (per 1,000 device days) | 2.3 | 5.6 | 0 | 11.2 | 6.8 | 6.6 | 0 | 0 |
| 3IN CAUTI Rate (per 1,000 device days) | 1.2 | 0 | 0 | 0 | 0 | 0 | 0 | 0 |
| 3IS CAUTI Rate (per 1,000 device days) | 4.7 | 0 | 9.8 | 0 | 0 | 0 | 0 | 0 |
| 4IN CAUTI Rate (per 1,000 device days) | 5.9 | 13.5 | 0 | 0 | 0 | 0 | 0 | 0 |
| 4IS CAUTI Rate (per 1,000 device days) | 0.9 | 0 | 0 | 0 | 0 | 0 | 0 | 0 |
| NHSN CAUTI Benchmark | 1.3 | 1.4 | 1.4 | 1.4 | 1.4 | 1.4 | 1.4 | 1.4 |

The hospital report also details information collected on the 1,282 patients over a three month period related to: (a) risk factors associated with CAUTIs, and (b) nurse behaviors related to care of Foley catheters. Data were collected for each patient for a period of 1 to 10 days depending on length of stay. Descriptive statistics were calculated in order to evaluate potential risk factors for CAUTI's, including age, gender, weight, stool incontinence, and related nursing practices among patients in critical care.

It should be recognized that sometimes an ICU held few catheterized patients and that multiple variables can impact CAUTI rate, including staff compliance with established protocol. For example, where there are few catheterized patients in the ICU, the CAUTI rate may fall to zero. However, overall, the impact of the protocol of the method of the invention is clearly demonstrated to reduce CAUTI rates and to increase compliance with the new protocol as compared to established protocol.

In order to evaluate nursing practice of Foley care, the following questions were asked of the nurses: 1) was THERAWORX® brand skin cleanser used to clean the perineum? 2) was THERAWORX® brand skin cleanser used to clean the Foley catheter? 3) were the components of the catheter accurately attached? and 4) was the Foley catheter accurately placed? The information relating to nursing practice of Foley care is summarized below in Table 2. The letter "n" refers to the number of device indwelling days.

TABLE 2

| Day in Hospital | Theraworx used to cleanse Perineum Yes(n) | Theraworx used to cleanse Foley Yes (n) | Accurate attachment of the device Yes(n) | Accurate placement of the Foley Yes(n) |
|---|---|---|---|---|
| 1 | 99.1% (1,099) | 99.8% (1,238) | 99.4% (1,238) | 99.8% (1,241) |
| 2 | 98.8% (811) | 100.0% (872) | 99.9% (874) | 99.9% (869) |
| 3 | 99.7% (385) | 99.8% (421) | 99.8% (422) | 100.0% (422) |
| 4 | 97.8% (223) | 99.6% (241) | 99.2% (241) | 100.0% (241) |
| 5 | 100.0% (113) | 100.0% (121) | 100.0% (120) | 100.0% (120) |
| 6 | 100.0% (56) | 100.0% (59) | 100.0% (59) | 100.0% (59) |
| 7 | 100.0% (15) | 100.0% (15) | 100.0% (15) | 100.0% (15) |
| 8 | 100.0% (5) | 100.0% (5) | 100.0% (5) | 100.0% (5) |
| 9 | 100.0% (3) | 100.0% (3) | 100.0% (3) | 100.0% (3) |
| 10 | no data | no data | no data | no data |

John Muir Medical Center in Walnut Creek, Calif., undertook a study as a quality improvement project in its emergency department, the study undertaken from April 2013 to Jul. 10, 2014, to evaluate the impact of THERAWORX® brand skin cleanser as an antiseptic used in protocols for urinary catheter insertion and maintenance for CAUTI prevention in hospitalized patients. CAUTI's were defined according to the definitions of the Centers for Disease Control and Prevention National Healthcare Safety Network. The John Muir study specifically refers to the Prevention Guidelines of the Healthcare Infection Control Practices Advisory Committee (HICPAC) and to Gould C. V., Umscheid C. A., Agarwal R. K., et al.

The "Guideline for Prevention of Catheter-Associated Urinary Tract Infections 2009," which was accessed by John Muir Medical Center in 2014, recommends, in contrast to the method of the invention studied at John Muir and the subject matter of the invention described herein, that antiseptic solutions not be used for routine catheter maintenance due to a lack of evidence to make an evidence-based decision. However, cleaning the periurethral area with antiseptics is recommended.

The John Muir Medical Center Study concluded that clear trends were evident shortly after use of the full THERAWORX® brand skin cleanser protocol was implemented that may show an effective CAUTI prevention intervention once fully implemented that is guideline concordant and fills critical gaps in knowledge.

The John Muir Medical Center protocol included using a cloth impregnated with Theraworx® brand antiseptic to wipe the perineum before Foley catheter insertion, concentrating on the entrance to the meatus, wiping front-to-back for women and in concentric circles around the glans penis for men. This first application was allowed to dry for thirty seconds and not rinsed off. Thereafter, the Foley catheter kit was opened, a BETADINE® brand antiseptic povidone/iodine formulation was applied with a swab to cleanse the urinary meatus area and the Foley catheter was inserted while practicing accepted sterile techniques. A new, second cloth impregnated with THERAWORX® brand skin cleanser was used to wipe around the meatus and catheter in a downward direction for post-insertion catheter care, again wiping front-to-back for women and in concentric circles around the glans penis for men. Thereafter, new fresh wipes or a foam solution applied to a clean washcloth were used for routine catheter care and frequent perineum care every 8 to 12 hours, all in accordance with the invention, and for final cleaning after each incidence of incontinence or other contaminating event. In the event high risk factors were identified, then maintenance was increased to every four hours until the catheter was removed.

Figure 4:
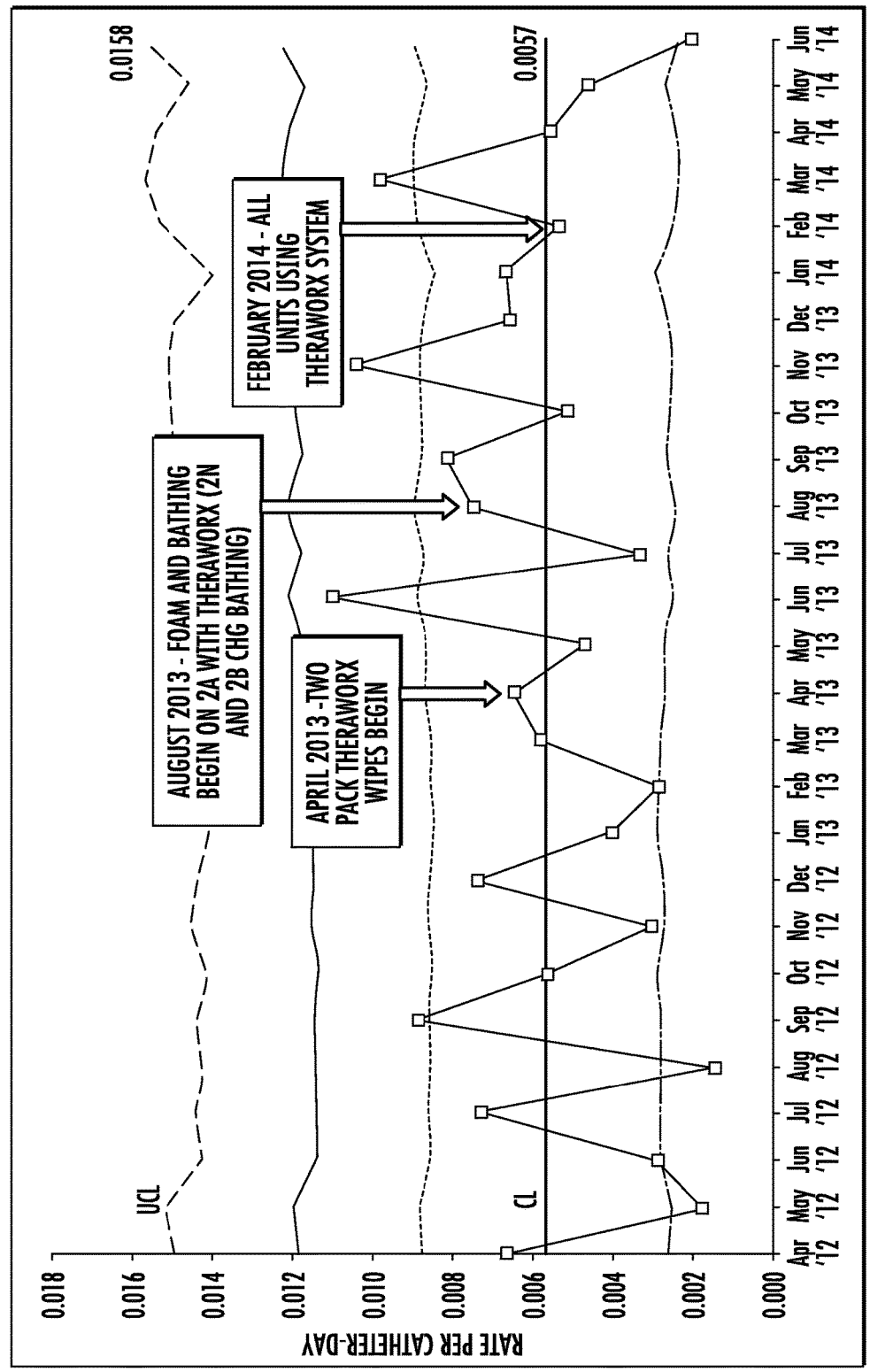
FIG. 4 is a statistical process control u-chart, which illustrates rates of CAUTI's over time from a Poisson distribution, taken from a hospital quality improvement project.
Figure 5:
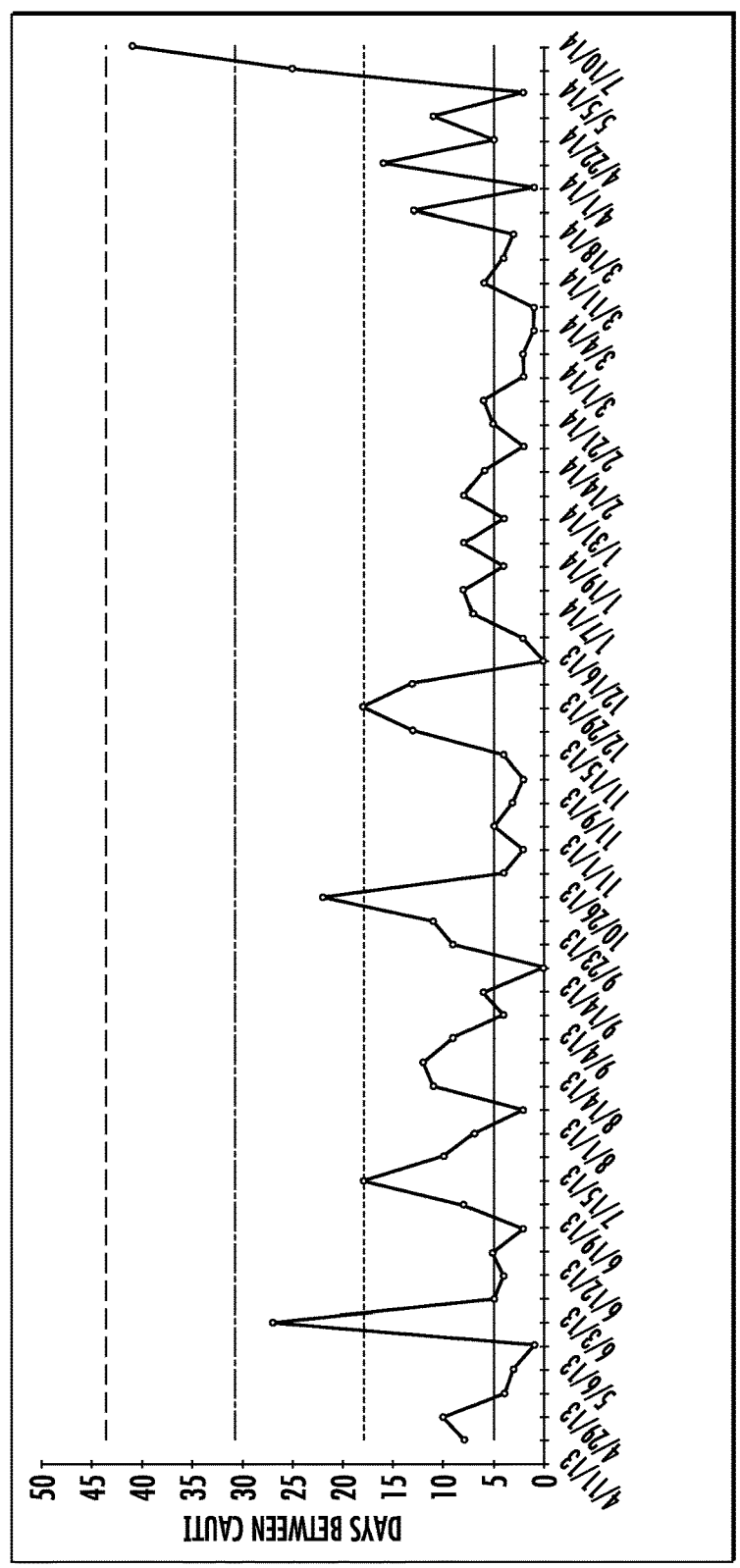
FIG. 5 illustrates intervals of time between CAUTI's, taken from a hospital quality improvement project.

FIG. 4 graphically illustrates the CAUTI rate per catheter day by month at the Walnut Creek facility for the period of the trial. FIG. 5 graphically illustrates the days between CAUTI's over time, by month.

John Muir Medical Center reported that use of cloths impregnated with THERAWORX® brand skin cleanser in connection with improvement in nursing staff behaviors drastically reduced the number of insertion-related CAUTI's, which are CAUTI's in which a UTI is not present on admission and a positive urine culture develops on or before the third day after insertion. In the four months after the improvements in quality were implemented, the number of documented emergency department related CAUTI went from 3 to less than 1.5 and costs dropped commensurately. In one month, the number of CAUTI's was zero, and no costs attributable to CAUTI were incurred.

Figure 6:
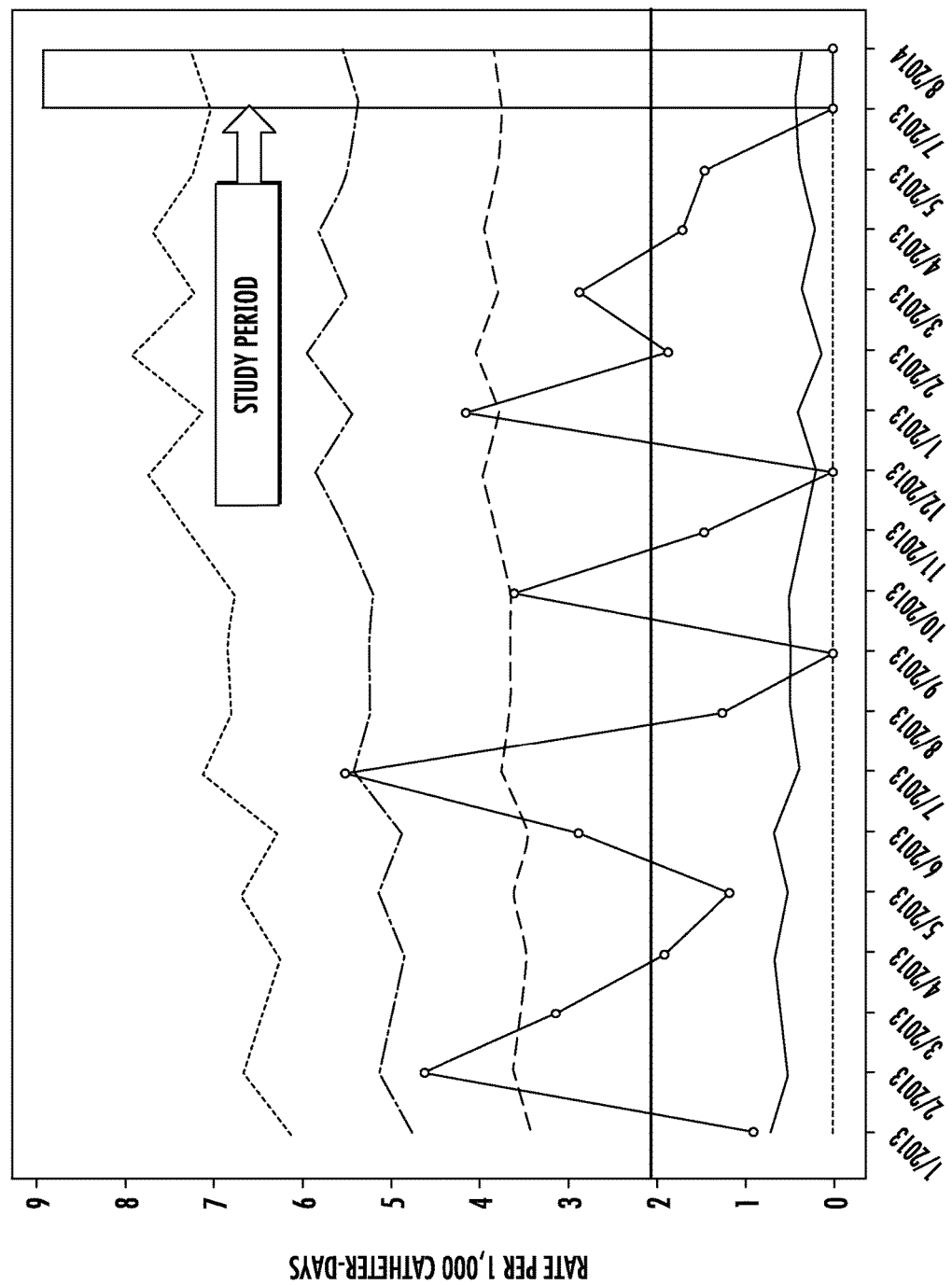
FIG. 6 is a statistical process control u-chart, which illustrates rates of CAUTI's over time from a Poisson distribution, taken from a different hospital quality improvement project of that illustrated in FIG. 4.

Euclid Hospital, a hospital in the Cleveland Clinic Hospital system, Cleveland Ohio, undertook a quality improvement project similar to that of John Muir Medical Center from June through August 2014, although June was considered to have been used for training in the protocol of the invention. The CAUTI rate from January 2013 to August 2014 is graphically illustrated in FIG. 6 as the result of a statistical analysis. Euclid Hospital stated that THERAWORX® brand skin cleanser and the protocol of the invention may be an effective CAUTI prevention intervention and that THERAWORX® brand skin cleanser's antiseptic benefits over other antiseptics includes a broad spectrum of activity, ability to maintain the skin's natural pH, which is to say to protect the stratum corneum, and being sufficiently mild for use in the peri-rectal areas and on mucus membranes. Although no special cause variation was identified on the statistical process control chart, FIG. 6, Euclid Hospital was able to reach and maintain zero CAUTI after implementation of the protocol of the invention.

Antiseptic solutions for use in the practice of the invention, including THERAWORX® brand skin cleanser, unlike cholorohexadrine and alcohol, have no restrictions for application to the face, mucus membranes, the meatus, or perineal and rectal areas, and may be used as frequently as deemed necessary. Formulations of this nature have broad-spectrum antimicrobial activity, anti-yeast and anti-fungal properties, while nourishing and moisturizing the skin, maintaining the natural pH of the skin's mantel, supporting the stratum corneum so that barrier function is preserved even as the skin is decolonized from infectious agents. Prolonged antimicrobial activity is demonstrated up to about three hours. It should be noted that odors are also one indication of infection and that practice of the method of the invention reduces or eliminates odors associated with CAUTI's. The mode of bacterial cellular death is believed to be disruption of cell membranes with the resultant loss of cytoplasmic contents and yet without damage to skin or living tissues. Three substances are believe to contribute: citrus-based antimicrobial stabilizers, zwitterionic surfactants with quaternary ammonium cations, and colloidal silver. The formulation contains vitamin E, aloe vera, allantoin, colloidal silver, and beta glucan 1, and is said to be greater than 99.9% effective against gram negative and gram positive bacteria.

The invention is defined as set forth in the appended claims.

What is claimed is:

1. A method for reducing the incidence of catheter associated urinary tract infections (CAUTI's) of the type acquired as a result of the use of an indwelling urinary catheter and in which a urinary catheter is inserted into a mammalian urethra thereby to define a urethral insertion site, the site having an indwelling urinary catheter, the indwelling urinary catheter characterized by an inserted catheter portion and an exposed catheter portion, the urethral insertion site defined by stratum corneum skin tissue having a barrier function and comprising a meatus, a surrounding perineum, and contiguous mucosa between the meatus and perineum, the method comprising the steps of:
   a. wiping the perineum, meatus, and contiguous mucosa surrounding a mammalian urethra for a urinary catheter insertion site with an antiseptic solution that is non-antibiotic and zwitterionic, has a pH of from about 4.4 to 5.5 and has properties of supporting the barrier function of stratum corneum skin tissue defining the insertion site;
   b. wiping the catheter with a solution of subpart (a);
   c. inserting the catheter wiped in accordance with step (b) into the urethra so as to define an indwelling catheter having an inserted catheter portion and an exposed catheter portion;
   d. wiping the exposed catheter portion of the indwelling catheter along with the perineum, meatus, and contiguous mucosa surrounding the insertion site immediately after step (c) of inserting the catheter and in a downward direction with the solution of subpart (a);
   e. wiping the exposed catheter portion and the perineum, meatus, and contiguous mucosa surrounding the insertion site periodically at least every 12 hours for an entire period of indwelling of the catheter with the solution of subpart (a);
   f. determining when the catheter is to be removed;
   g. wiping the perineum, meatus, and contiguous mucosa surrounding the insertion site with the solution of subpart (a) immediately prior to catheter removal;
   h. removing the catheter following step (g); and
   i. wiping the perineum, meatus, and contiguous mucosa surrounding the insertion site with the solution of subpart (a) immediately after catheter removal.

2. The method of claim 1 further comprising wiping the meatus with a povidone-iodine solution before inserting the catheter in accordance with step (c).

3. The method of claim 1 wherein the solution of subpart (a) comprises citrus-based antimicrobial stabilizers, zwitterionic surfactants with quaternary ammonium ions, and colloidal silver.

4. The method of claim 1 wherein the solution of subpart (a) has a pH of from about 4.7 to 5.5.

5. The method of claim 1 wherein the solution of subpart (a) is an aqueous composition comprising at least one surfactant, at least one anti-inflammatory agent, at least one non-foaming agent, at least one cell growth promoting agent, at least one fast acting antimicrobial agent, and at least one different ingredient selected from the group consisting of immune system enhancing agents, absorption facilitating agents, humectants and emollients, free radical scavenging agents, and healing promoting agents.

6. The method of claim 1 in which the wiping step (e) is repeated about every 6 to 8 hours.

7. The method of claim 1 wherein the wiping step (e) is repeated about every 4 hours.

8. The method of claim 1 further comprising the step of, after removing the catheter wiping the perineum, meatus, and contiguous mucosa surrounding the insertion site with the solution of subpart (a) at an interval of about every 6 to 12 hours during a period of about 5 days to up to a month.

9. The method of claim 8 wherein the step of wiping the perineum, meatus, and contiguous mucosa surrounding the insertion site with the solution of subpart (a) after removing the catheter is repeated about every 6 to 12 hours for from about 5 to 7 days.

10. The method of claim 8 wherein steps (a) through (i) are performed in a health care setting and the method further comprises the step after step (i) of providing a kit for home care for wiping the perineum, meatus, and contiguous mucosa surrounding the insertion site with the solution of subpart (a) after removing the catheter.

11. The method of claim 1 further comprising repeating step (e) after an incidence of incontinence or other contamination.

12. The method of claim 1 wherein step (e) is repeated every 4 hours in the event of the occurrence of risk factors.

\* \* \* \* \*